US008808357B2

(12) United States Patent
Shalaby et al.

(10) Patent No.: US 8,808,357 B2
(45) Date of Patent: Aug. 19, 2014

(54) RADIOPAQUE IODINATED AND IODIDE-CONTAINING CRYSTALLINE ABSORBABLE ALIPHATIC POLYMERIC MATERIALS AND APPLICATIONS THEREOF

(75) Inventors: Shalaby W. Shalaby, Anderson, SC (US); Kenneth David Gray, Clemson, SC (US)

(73) Assignee: Poly-Med, Inc., Anderson, SC (US)

( * ) Notice: Subject to any disclaimer, the term of this patent is extended or adjusted under 35 U.S.C. 154(b) by 325 days.

(21) Appl. No.: 12/798,461

(22) Filed: Apr. 6, 2010

(65) Prior Publication Data

US 2011/0245912 A1 Oct. 6, 2011

(51) Int. Cl.

| | | |
|---|---|---|
| A61F 2/06 | (2013.01) | |
| A61F 2/00 | (2006.01) | |
| C08G 64/02 | (2006.01) | |
| C08G 63/682 | (2006.01) | |
| C09D 167/04 | (2006.01) | |
| C08G 18/73 | (2006.01) | |
| C08G 18/46 | (2006.01) | |
| C09D 169/00 | (2006.01) | |

(52) U.S. Cl.
CPC ........ *C08G 63/6822* (2013.01); *C08G 64/0233* (2013.01); *C09D 167/04* (2013.01); *C08G 18/73* (2013.01); *C08G 18/4607* (2013.01); *C09D 169/00* (2013.01)
USPC .......................................... 623/1.34; 424/423

(58) Field of Classification Search
USPC ......... 623/1.13, 1.34, 1.44–1.54, 23.66, 1.32, 623/1.33; 604/8, 9; 428/296.7; 424/423
See application file for complete search history.

(56) References Cited

U.S. PATENT DOCUMENTS

| | | | | |
|---|---|---|---|---|
| 4,656,224 A * | 4/1987 | Larsen | 525/40 |
| 5,415,546 A * | 5/1995 | Cox, Sr. | 433/213 |
| 5,543,158 A * | 8/1996 | Gref et al. | 424/501 |
| 5,652,053 A * | 7/1997 | Liegeois | 442/150 |
| 5,731,402 A * | 3/1998 | Nishida et al. | 528/222 |
| 6,013,340 A * | 1/2000 | Bonk et al. | 428/35.2 |
| 6,013,855 A * | 1/2000 | McPherson et al. | 623/23.76 |
| 6,174,330 B1 * | 1/2001 | Stinson | 623/1.34 |
| 6,174,602 B1 * | 1/2001 | Matsui et al. | 428/373 |
| 6,248,057 B1 * | 6/2001 | Mavity et al. | 600/3 |
| 6,355,058 B1 * | 3/2002 | Pacetti et al. | 623/1.15 |
| 6,426,145 B1 * | 7/2002 | Moroni | 428/412 |
| 6,444,217 B1 * | 9/2002 | Kwok et al. | 424/423 |
| 6,569,528 B2 * | 5/2003 | Nam et al. | 428/402 |
| 6,579,617 B2 * | 6/2003 | Matsui et al. | 428/364 |
| 6,811,776 B2 * | 11/2004 | Kale et al. | 424/93.7 |
| 6,844,062 B2 * | 1/2005 | Matsui et al. | 428/370 |
| 6,861,503 B2 * | 3/2005 | Shalaby | 528/425 |
| 7,026,374 B2 * | 4/2006 | Nathan et al. | 523/113 |
| 7,229,826 B2 * | 6/2007 | Kale et al. | 435/372 |
| 7,371,575 B2 * | 5/2008 | Kale et al. | 435/372 |
| 7,465,489 B2 * | 12/2008 | Shalaby et al. | 428/296.7 |
| 7,553,325 B2 * | 6/2009 | Stinson | 623/1.34 |
| 7,935,143 B2 * | 5/2011 | Wang | 623/1.42 |
| 7,964,207 B2 * | 6/2011 | Deslauriers et al. | 424/423 |
| 7,993,411 B2 * | 8/2011 | Kennedy et al. | 623/23.7 |
| 8,043,367 B2 * | 10/2011 | Wang | 623/1.42 |
| 8,083,806 B2 * | 12/2011 | Shalaby et al. | 623/23.66 |
| 8,211,458 B2 * | 7/2012 | Deslauriers et al. | 424/422 |
| 8,252,887 B2 * | 8/2012 | Bolikal et al. | 528/206 |
| 8,415,449 B2 * | 4/2013 | Kohn et al. | 528/203 |
| 8,476,399 B2 * | 7/2013 | Bolikal et al. | 528/206 |
| 2004/0001890 A1 * | 1/2004 | Rosenblatt et al. | 424/469 |
| 2004/0229353 A1 * | 11/2004 | Kale et al. | 435/366 |
| 2005/0261756 A1 * | 11/2005 | Siren | 623/1.15 |
| 2005/0287216 A1 * | 12/2005 | Loomis | 424/486 |
| 2006/0020331 A1 * | 1/2006 | Bates et al. | 623/1.49 |
| 2007/0099819 A1 * | 5/2007 | Glidden | 514/2 |
| 2007/0208420 A1 * | 9/2007 | Ameer et al. | 623/1.41 |
| 2008/0213611 A1 * | 9/2008 | Asgari | 428/566 |
| 2008/0249638 A1 * | 10/2008 | Asgari | 623/23.75 |
| 2008/0269874 A1 * | 10/2008 | Wang et al. | 623/1.34 |
| 2009/0171449 A1 * | 7/2009 | Wang | 623/1.34 |
| 2009/0175924 A1 * | 7/2009 | Siren | 424/423 |
| 2009/0177286 A1 * | 7/2009 | Shalaby et al. | 623/23.7 |
| 2009/0233887 A1 * | 9/2009 | Shalaby et al. | 514/154 |
| 2009/0259125 A1 * | 10/2009 | Stinson | 600/431 |
| 2009/0259297 A1 * | 10/2009 | Wang | 623/1.34 |
| 2009/0306120 A1 * | 12/2009 | Lim et al. | 514/291 |
| 2010/0055428 A1 * | 3/2010 | Kim et al. | 428/213 |
| 2010/0303879 A1 * | 12/2010 | Kurdyumov et al. | 424/422 |
| 2010/0316687 A1 * | 12/2010 | Swan et al. | 424/422 |
| 2011/0022161 A1 * | 1/2011 | Uhrich et al. | 623/1.46 |
| 2011/0076314 A1 * | 3/2011 | Kurdyumov | 424/422 |
| 2011/0104052 A1 * | 5/2011 | Barnett et al. | 424/1.21 |
| 2011/0159067 A1 * | 6/2011 | Rolfes Meyering | 424/422 |
| 2011/0245912 A1 * | 10/2011 | Shalaby et al. | 623/1.34 |
| 2011/0274645 A1 * | 11/2011 | Sendijarevic et al. | 424/78.37 |
| 2011/0275782 A1 * | 11/2011 | Kohn et al. | 528/208 |
| 2012/0197001 A1 * | 8/2012 | Kohn et al. | 528/203 |
| 2012/0208789 A1 * | 8/2012 | Shalaby et al. | 514/152 |
| 2012/0226013 A1 * | 9/2012 | Kohn et al. | 528/292 |
| 2012/0302719 A1 * | 11/2012 | Kohn et al. | 528/208 |
| 2013/0085238 A1 * | 4/2013 | Bolikal et al. | 525/450 |
| 2013/0225778 A1 * | 8/2013 | Goodrich et al. | 526/270 |

OTHER PUBLICATIONS

Matweb, Polyglycolic Acid (PGA), Aug. 10, 2012, Matweb Material Property Data web page, 1 page.*
Sawai et al, Crystal Density and Heat of Fusion for a Stereo-Complex of Poly(L-Lactic acid) and Poly(D-Lactic acid), Jun. 17, 2007, Wiley InterScience, pp. 2632-2639.*
Nottelet et al, Synthesis of an X-ray opaque biodegradable copolyester by chemical modification of poly(E-caprolactone), Jun. 6, 2006, Elsevier, Biomaterials, pp. 4948-4954.*

* cited by examiner

*Primary Examiner* — Alvin Stewart

(57) ABSTRACT

Radiopaque, iodinated, absorbable polyesters, polyester urethanes, and polyether-ester-urethanes with and without inorganic iodide micro-/nanoparticles dispersed or solubilized therein, and composite inorganic iodide micro-/nanoparticles in an absorbable polyester, polyester-urethane, polyester-ester, or polyether-ester urethane matrix are employed in medical devices and therapeutic compositions.

14 Claims, No Drawings

RADIOPAQUE IODINATED AND IODIDE-CONTAINING CRYSTALLINE ABSORBABLE ALIPHATIC POLYMERIC MATERIALS AND APPLICATIONS THEREOF

FIELD OF THE INVENTION

The present invention is directed to iodine-bearing, absorbable polymeric compositions and inorganic, iodide-containing absorbable polymers and applications thereof in preparing absorbable radiopaque, melt-extruded monofilaments, electrostatically spun microfibers, surface coatings, and radiographic markers, which can, in turn, be used individually or in combination for assembling radiographically detectable medical devices and controlled release drug delivery systems.

BACKGROUND OF THE INVENTION

Until recently, imparting radiopacity to medical devices and polymeric materials therefore was limited to incorporating sufficient amounts of radiopaque, insoluble inorganic microparticles of heavy metal salts or oxides, as in the case of the use of barium sulfate in polymethyl methacrylate bone cement (Damian & Shalaby, U.S. Pat. No. 5,795,922) and several types of non-absorbable, non-crystalline polymeric materials such as those based on silicones and polyurethanes. In recent years, the concept of producing inorganic-organic hybrid fibers comprising insoluble radiopaque, inorganic microparticles and crystalline polymeric components was used by one of the present inventors and coworkers to produce medical devices in order to (1) impart radiopacity in melt-spun monofilaments (U.S. Pat. No. 7,465,489 and U.S. Pat. application Ser. No. 11/880/993); (2) impart radiopacity in electrostatically spun microfibers (U.S. Pat. application Ser. No. 11/599,695); and (3) not only impart radiopacity but also contribute to a timely disintegration/absorption of a load-bearing component in an absorbable/disintegratable ureteral stent (PCT Application Serial No. 06/03619 and U.S. Pat. application Ser. No. 11/346,117). Meanwhile, there has been some interest in preparing iodine-bearing, non-crystalline materials, including absorbable polymers. Most relevant to the instant invention are those which entailed the preparation of polymers with the iodine atom attached to an aromatic side group in the polymer chains (U.S. Pat. No. 6,475,477). To date, the lack of interest in developing or even exploring iodine-containing crystalline, aliphatic polymers of commercial interest in the medical industry is not surprising. This is because of the perceived limitations associated with the conditions used in preparing those polymers or iodide-containing radiopaque polymer blends, which can compromise the stability of the iodine-bearing additive or intermediates. This, and the lack of crystalline absorbable polymers useful for use in preparing radiopaque medical devices and coatings as well as radiographic markers by virtue of having sufficient amounts of iodine-containing species therein, provided an incentive to pursue the study, subject of the instant invention. Accordingly, this invention is directed to (1) the preparation of new, 80-100% aliphatic, absorbable, crystalline iodinated polymers for use as coatings and radiographic markers for medical devices; (2) the preparation of melt-extrudable hybrid composites into microfilament, monofilament, and multifilament yarns of water-soluble inorganic iodide salt and absorbable copolyester; (3) devices made of the above-noted radiopaque monofilament and multifilament yarns and radiopaque coatings; and (4) devices analogous to the above-noted ones comprising a radioactive iodine isotope (e.g., iodine-131 or 123) for use as pharmacokinetic markers and in radiation therapy.

SUMMARY OF THE INVENTION

Accordingly, the present invention is directed to a radiopaque, iodinated, crystalline, aliphatic, absorbable polyester having a molecular weight exceeding 5 kDa, preferably exceeding 15 kDa, more preferably exceeding 25 kDa, most preferably exceeding 50 kDa and a heat of fusion of at least 10 J/g, preferably at least 20 J/g, more preferably at least 30 J/g, most preferably at least 40 J/g, wherein the polyester is the reaction product of an iodohydroxylic or iodo-substituted amine initiator, and at least one monomer selected from the group consisting of l-lactide, glycolide, trimethylene carbonate, p-dioxanone, 1,5-dioxepan-2-one, $\epsilon$-caprolactone, and a morpholinedione under typical ring-opening polymerization conditions, using an organometallics catalyst.

A specific aspect of this invention deals with a radiopaque, iodinated, crystalline, 80-100% aliphatic, absorbable polyester having a molecular weight exceeding 5 kDa, preferably exceeding 15 kDa, more preferably exceeding 25 kDa, most preferably exceeding 50 kDa, and a heat of fusion of at least 10 J/g, preferably at least 20 J/g, more preferably at least 30 J/g, most preferably at least 40 J/g, in the form of a radiopaque coating, part of a higher molecular coating, radiographically detectable marker, or a component in at least one medical device, wherein the at least one medical device is selected from the group consisting of an absorbable/disintegratable urinogenital stent, an absorbable endovascular stent, absorbable diagnostic device, and absorbable barrier film to protect surrounding tissue from low level radiation associated with Brachy therapy, or treatment for abdominal and ovarian cancer, and an absorbable diagnostic device.

Another specific aspect of this invention deals with a radiopaque, iodinated, crystalline, 80-100% aliphatic, absorbable polyester having a molecular weight exceeding 5 kDa, preferably exceeding 15 kDa, more preferably exceeding 25 kDa, most preferably exceeding 50 kDa, and a heat of fusion of at least 10 J/g, preferably at least 20 J/g, more preferably at least 30 J/g, most preferably at least 40 J/g, wherein the polyester is the reaction product of an iodohydroxylic initiator, and at least one monomer selected from the group consisting of l-lactide, glycolide, trimethylene carbonate, p-dioxanone, 1,5-dioxepan-2-one, $\epsilon$-caprolactone, and a morpholinedione under typical ring-opening polymerization conditions, using an organometallics catalyst, and wherein the polyester chains are covalently interlinked with a urethane group to increase its molecular weight to a value exceeding 8 kDa. In effect, the interlinked chains are the reaction product of a hydroxy-terminated iodinated polyester and an aliphatic diisocyanate selected from the group consisting of 1,6-hexane-diisocyanate, 1,4-bis(methylene isocyanato) cyclohexane, 1,6-cyclohexane diisocyanate, 1,4-tetramethylene diisocyanate, and lysine diisocyanate and the respective products can be used in the form of a radiopaque coating, part of a higher molecular coating, radiographically detectable marker, or a component in at least one medical device, wherein the at least one medical device is selected from the group consisting of an absorbable/disintegratable urinogenital stent, an absorbable endovascular stent, an absorbable device for treating aneurysm, a device for treating prostatic cancer, and an absorbable diagnostic device.

A clinically important aspect of this invention deals with a radiopaque, iodinated, crystalline, 80-100% aliphatic, absorbable polyester having a molecular weight exceeding 5 kDa, preferably exceeding 15 kDa, more preferably exceeding 25 kDa, most preferably exceeding 50 kDa, and a heat of fusion of at least 10 J/g, preferably at least 20 J/g, more preferably at least 30 J/g, most preferably at least 40 J/g, wherein the iodine component is iodine-127. Collectively, the simple iodinated products and their radioactive counterparts (using iodine 123 or 131) are suitable for use in therapeutic, site-specific applications.

Another major aspect of this invention deals with a radiopaque, absorbable composite of at least one type of inorganic iodo-compound micro-/nanoparticles dispersed or solubilized in an organic absorbable crystalline matrix having a molecular weight of at least 5 kDa, preferably exceeding 15 kDa, more preferably exceeding 25 kDa, most preferably exceeding 50 kDa, and a heat of fusion exceeding 10 J/g, preferably at least 20 J/g, more preferably at least 30 J/g, most preferably at least 40 J/g, wherein the at least one type of inorganic iodo-compound micro-/nanoparticles represent 10 to 70 percent of the total mass of the composite, wherein the organic absorbable crystalline matrix is (1) an absorbable polyester derived from at least one cyclic monomer selected from the group consisting of l-lactide, glycolide, trimethylene carbonate, p-dioxanone, 1,5-dioxepan-2-one, ϵ-caprolactone, and a morpholinedione, and wherein the organic absorbable crystalline matrix is selected from the reaction product of an iodohydroxylic initiator, and at least one monomer selected from the group consisting of l-lactide, glycolide, trimethylene carbonate, p-dioxanone, 1,5-dioxepan-2-one, ϵ-caprolactone, and a morpholinedione under typical ring-opening polymerization conditions, using an organometallics catalyst; and (2) the reaction product from item 1 covalently interlinked with a urethane group to increase its molecular weight to a value exceeding 8 kDa—the interlinking can be achieved using an aliphatic diisocyanate selected from the group consisting of 1,6-hexane-diisocyanate, 1,4-bis(methylene isocyanato) cyclohexane, 1,6-cyclohexane diisocyanate, 1,4-tetramethylene diisocyanate, and lysine diisocyanate.

A second clinically important aspect of this invention deals with a radiopaque, absorbable composite of at least one type of inorganic iodo-compound micro-/nanoparticles dispersed or solubilized in an organic absorbable crystalline matrix having a molecular weight of at least 5 kDa, preferably exceeding 15 kDa, more preferably exceeding 25 kDa, most preferably exceeding 50 kDa, and a heat of fusion exceeding 10 J/g, preferably at least 20 J/g, more preferably at least 30 J/g, most preferably at least 40 J/g, wherein said product is in the form of a coating, part of a higher molecular weight coating, radiographically detectable marker, or component of at least one medical device, and wherein the at least one medical device is selected from the group consisting of an absorbable/disintegratable urinogenital stent, absorbable endovascular stent, an absorbable device for treating aneurysm, a device for treating prostatic, lung (Brachy therapy), ovarian or intestinal cancers, and an absorbable diagnostic device, and further wherein the iodo-compound comprises iodine-127. Collectively, these composite products and their radioactive counterparts are suitable for use in therapeutic, site-specific applications.

A technologically important aspect of this invention deals with all compositions described herein, processed into at least one fibrous form selected from the group consisting of electrospun non-woven microfibers, melt-extruded monofilament and multifilament yarns, melt-extruded tubes, and catheters.

DETAILED DESCRIPTION OF PREFERRED EMBODIMENTS

Generally, the present invention is directed to totally absorbable/dissolvable radiopaque compositions for use in pharmaceutical and biomedical applications, wherein the radiopacity is due to the presence of an iodine or bromine atom that is covalently linked to the molecular chain of an absorbable polymer and/or the presence of at least one water-soluble micro-/nanoparticulate iodide or bromide salt selected from those comprising an alkaline or alkaline earth metal atom, preferably sodium iodide, potassium iodide, and magnesium iodide. For the absorbable polymers comprising iodine or bromine atom-bearing chains, there can be more than one of such atoms per molecular chain. The respective absorbable chains may comprise at least one type of ester linkage. Other chemical linkages can be present in those chains and can be selected from the group consisting of an aliphatic carbonate, acyclic carbonate, cycloaliphatic urethane, acyclic aliphatic urethane, cycloaliphatic carbonate, aliphatic ether, and aliphatic anhydride.

Typical applications of iodine-bearing absorbable polymers (referred to herein as "iodinated polymers") and/or soluble iodide micro-/nanoparticles include: (1) surface coatings for catheters, particularly those used percutaneously; (2) absorbable constructs for site-specific diagnostic applications; (3) components of absorbable/disintegratable endovascular and urinogenital stents; (4) catheters for deploying radioactive compositions for treating cancer as in the case of iodine-131 (or 123) in the treatment of prostate, lung, intestinal or ovarian cancers; (5) dosage forms for the controlled delivery of iodide in the treatment of thyroid glands and particularly in the case of accidental exposure to radioactive iodine; (6) components of an absorbable device or pharmaceutical product to monitor its pharmacokinetics using iodine-127, 123 or 131; and (7) barrier film to protect surrounding tissues during Brachy therapy and similar radiotherapies as in the treatment of ovarian and abdominal cancers.

Technologically and clinically important aspects of the instant invention deal with (1) the production of hybrid composites by melt-processing or solution casting of water-soluble inorganic radiopaque iodide salt dispersed in an absorbable thermoplastic polyester, polyether-ester, segmented copolyester, segmented polyether-ester, segmented polyester-urethane, and polyether-ester urethane; (2) the use of at least one of the hybrid composites in item 1 in at least one type of controlled drug release system selected from the group consisting of implantable monofilaments, microspheres, solid-suspensions, and viscous polymeric liquids; (3) the extrusion of at least one composite of item 1 into microfilament, monofilament, multifilament yarns and films, which can be used in several applications including the construction of surgical sutures, endovascular stents, perivascular wraps, hemostatic devices, blocking devices, retraction tapes, and endovascular devices for treating aneurysms; (4) electrostatic spinning of solutions of composites in item 1 into non-woven micro-/nano-fibrous fabrics or constructs which can be used as pledgets and components thereof, hemostatic felts, drug delivery systems, and antimicrobial cuffs for catheters; (5) the preparation of surface coatings to enhance or impart radiopacity of any of the surgical devices noted in items 1-4; and (6) the use of combinations of the radiopaque microparticles and radiopaque iodinated polymers of items 1 & 2 for the production of medical devices and the pharmaceutical products described in items 3-5. Further illustrations of the present invention are provided by the following examples:

EXAMPLE 1

Preparation of a Typical Highly Iodinated Absorbable Polyester: PI-1

L-lactide (0.5901 mol, 85.0 grams, 82% by mol), glycolide (0.1295 mol, 15.0 grams, 18% by mol), and 3-iodo-1-propanol (0.01799 mol, 3.346 grams) were added to a flame-dried reaction flask fitted with a stainless steel stir rod. Low pressure (0.1-0.5 mmHg) was applied to the reaction setup for 30 minutes to 1 hour while heating in a silicone oil bath at 40° C. The system was purged with nitrogen gas, a stirrer bearing was attached to the mechanical stirrer, and the temperature of the system was raised to 140° C. to melt the monomer while stirring under a nitrogen atmosphere. Following the complete mixing of molten lactide and glycolide monomers with an initiator at high temperature, the temperature was reduced to 100° C. Subsequently, tin-2-ethylhexanoate ($6 \times 10^{-5}$ mol, 0.2 molar in toluene) was added at 100° C., and the reaction was mixed thoroughly before increasing the temperature to 135° C. to begin polymerization. The reaction was stirred for approximately 4.5 hours at 130-135° C., followed by continued polymerization at 135° C. for 60-70 hours without stirring. The reaction flask contents were allowed to cool to room temperature and the polymer was isolated. Samples of the isolated polymer were analyzed for molecular weight, identity, and thermal properties using standard GPC, IR, and DSC protocols, respectively.

EXAMPLE 2

Preparation of a Typical Moderately Iodinated Absorbable Polyester: PI-2

L-lactide (0.5901 mol, 85.0 grams, 82% by mol), glycolide (0.1295 mol, 15.0 grams, 18% by mol), and 3-iodo-1-propanol (0.01439 mol, 2.677 grams) were added to a flame-dried reaction flask fitted with a stainless steel stir rod. Low pressure (0.1-0.5 mmHg) was applied to the reaction setup for 30 minutes to 1 hour while heating in a silicone oil bath at 40° C. The system was purged with nitrogen gas, a stirrer bearing was attached to the mechanical stirrer, and the temperature of the system was raised to 140° C. to melt the monomer while stirring under a nitrogen atmosphere. Following the complete mixing of molten lactide and glycolide monomers with initiator at high temperature, the temperature was reduced to 100° C. Subsequently, tin-2-ethylhexanoate ($6 \times 10^{-5}$ mol, 0.2 molar in toluene) was added at 100° C., and the reaction was mixed thoroughly before increasing the temperature to 135° C. to begin polymerization. The reaction was stirred for approximately 4.5 hours at 130-135° C., followed by continued polymerization at 135° C. for 60-70 hours without stirring. The reaction flask contents were allowed to cool to room temperature and the polymer was isolated. Samples of the isolated polymer were analyzed for molecular weight, identity, and thermal properties using standard GPC, IR, and DSC protocols, respectively.

EXAMPLE 3

Preparation of a Typical Iodinated Urethane-interlinked Absorbable Polyester: PI-3

The radiopaque lactide/glycolide copolymer, initiated with 3-iodo-1-propanol($3.05 \times 10^{-3}$ mol, 50.1 grams), was added to a flame-dried reaction kettle fitted with a mechanical stirrer, a distillation neck and a collection flask. The polymer was dissolved in dichloromethane (0.5 g/ml) and mixed thoroughly with the mechanical stirrer at room temperature. Then 1,6-diisocyanatohexane ($1.527 \times 10^{-3}$ moles, 0.257 grams) was added to the reaction (1 mole of 1,6-diisocyanatohexane per 2 moles polymer) and the temperature was increased to 150° C. for 1-2 hours to react and to distill off the solvent. Upon cooling to room temperature, the resulting linked polymer was dissolved in dichloromethane (25% wt/vol), and 5 milliliters of isopropyl alcohol was added to the solution to quench any unreacted 1,6 diisocyanatohexane. Subsequently, the solution was precipitated in chilled isopropyl alcohol and filtered. The purified polymer was then dried at room temperature and reduced pressure. Samples of the isolated polymer were isolated and analyzed for molecular weight, identity, and thermal properties using standard GPC, IR, and DSC protocols, respectively.

EXAMPLE 4

Preparation and Evaluation of Radiopaque Films of PI-1 (from Example 1)

Films were prepared by a solvent-casting technique by first dissolving PI-1 in a mixture of 1:1 dichloromethane:chloroform at a concentration of 5-w/v%. The polymer solution was transferred to a glass container to allow solvent evaporation, resulting in a film (PI-1F1)of 0.2 mm thickness.

Preparation of Films from PI-1 containing 10% NaI was performed by dissolving 2.7 g PI-1 and 0.3g NaI in 6O mL of trifluoroethanol. The dissolved solution was transferred to a glass container to allow solvent evaporation, resulting in a film (PI-1F2) of 0.2 mm thickness.

Radiopacity of both films (PI-1F1 and PI-1F2) was verified using a Tingle model 325 M Veterinary X-ray unit with an EKLIN model EDR5-MKV processor.

EXAMPLE 5

Electrospinning of PI-1 (from Example 1) to Radiopaque Non-woven Microfibers

Electrospinning was accomplished on an electrospinning unit constructed in-house from a solution containing approximately 25-w/v% PI-1 in 1:1 dichloromethane: chloroform. Electrospinning was conducted using the following conditions: +5.6 kV charge at needle tip, −8.7kV charge at collection rod, +5kV at directional rings, 18 G blunt end needle, 0.25 mL/min flow rate, and 18 cm tip-to-collector distance. The electrospun fabric was comprised of microfibers having an average diameter of 5 micron.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicant hereby discloses all subranges of all ranges disclosed herein. These subranges are also useful in carrying out the present invention.

What is claimed is:

1. A radiopaque, iodinated, crystalline, 80-100% aliphatic, absorbable polyester, wherein the polyester is the reaction product of an iodohydroxylic initiator, and at least one monomer selected from the group consisting of l-lactide, glycolide, trimethylene carbonate, p-dioxanone, 1,5-dioxepan-2-one, ϵ-caprolackme, and a morpholinedione, the polyester having a molecular weight exceeding 5 kDa, a heat of fusion of at least 10 J/g.

2. A radiopaque, iodinated, crystalline, 80-100% aliphatic, absorbable polyester as in claim 1 in a form selected from the group consisting of a radiopaque coating, part of a higher molecular coating, a radiographically detectable marker, and a component in at least one medical device.

3. A radiopaque, iodinated, crystalline, 80-100% aliphatic, absorbable polyester as in claim 2 wherein the at least one medical device is selected from the group consisting of an absorbable/disintegratable urinogenital stent, an absorbable endovascular stent, and an absorbable diagnostic device.

4. A radiopaque, iodinated, crystalline, 80-100% aliphatic, absorbable polyester as in claim 1 covalently interlinked with a urethane group and having a molecular weight of greater than 8 kDa.

5. A radiopaque, iodinated, crystalline, 80-100% aliphatic, absorbable polyester as in claim 4 comprising the reaction product of a hydroxy-temiinated iodinated polyester and an aliphatic diisocyanate selected from the group consisting of 1,6-hexane-diisocyanate, 1,4-bis(methylene isocyanato) cyclohexane, 1,6-cyclohexane diisocyanate, 1,4-tetramethylene diisocyanate, and lysine diisocyanate.

6. A radiopaque, iodinated, 80-100% crystalline, aliphatic, absorbable polyester as in claim 4 in a form selected from a radiopaque coating, part of a higher molecular coating, a radiographically detectable marker, and a component in at least one medical device.

7. A radiopaque, iodinated, crystalline, 80-100% aliphatic, absorbable polyester as in claim 6 wherein the at least one medical device is selected from the group consisting of an absorbable/ disintegratable urinogenital stent, an absorbable endovascular stent, an absorbable device for treating aneurysm, a device for treating prostatic cancer, and an absorbable diagnostic device.

8. A radiopaque, iodinated, crystalline, 80-100% aliphatic, absorbable polyester as in claim 1 wherein the iodine component comprises iodine-127.

9. A radiopaque, iodinated, crystalline, 80-100% aliphatic, absorbable polyester as in claim 8 for use in therapeutic, site-specific applications.

10. A radiopaque, iodinated, crystalline, 80-100% aliphatic, absorbable polyester as in claim 1 for use in therapeutic, site-specific applications.

11. A composition which consists essentially of the radiopaque, iodinated, crystalline, 80-100% aliphatic, absorbable polyester of claim 1.

12. A method of preparing a radiopaque, iodinated, crystalline, 80-100% aliphatic, absorbable polyester which comprises reacting an iodohydroxylic initiator and at least one monomer selected from the group consisting of l-lactide, glycolide, trimethylene carbonate, p-dioxanone, 1,5-dioxepan-2-one, $\epsilon$-caprolactone, and a morpholinedione.

13. The method of claim 12 which further comprises reacting the hydroxy-terminated iodinated polyester and an aliphatic diisocyanate selected from the group consisting of 1,6-hexane-diisocyanate, 1,4-bis(methylene isocyanato) cyclohexane, 1,6-cyclohexane diisocyanate, 1,4-tetramethylene diisocyanate, and lysine diisocyanate.

14. A method of preparing a radiopaque, iodinated, crystalline, 80-100% aliphatic, absorbable polyester which consists essentially of reacting an iodohydroxylic initiator and at least one monomer selected from the group consisting of l-lactide, glycolide, trimethylene carbonate, p-dioxanone, 1,5-dioxepan-2-one, $\epsilon$-caprolactone, and a morpholinedione.

* * * * *